US008529254B2

(12) United States Patent
Millstein et al.

(10) Patent No.: US 8,529,254 B2
(45) Date of Patent: Sep. 10, 2013

(54) METHOD AND APPARATUS FOR OCCLUSAL POSITION MEASUREMENT AND RECORDING

(76) Inventors: Philip L. Millstein, Cambridge, MA (US); Edward W. Merrill, Belmont, MA (US)

( * ) Notice: Subject to any disclaimer, the term of this patent is extended or adjusted under 35 U.S.C. 154(b) by 19 days.

(21) Appl. No.: 13/302,190

(22) Filed: Nov. 22, 2011

(65) Prior Publication Data

US 2012/0092679 A1    Apr. 19, 2012

Related U.S. Application Data

(63) Continuation-in-part of application No. 12/256,171, filed on Oct. 22, 2008, now Pat. No. 8,066,512.

(51) Int. Cl.
*A61C 19/00* (2006.01)
*A61C 9/00* (2006.01)
*A61C 19/04* (2006.01)
*A61K 6/10* (2006.01)

(52) U.S. Cl.
USPC ............... 433/68; 433/34; 433/38; 433/214; 523/109

(58) Field of Classification Search
USPC ............... 433/34–48, 213–215, 68–71, 226, 433/228.1; 523/109; 249/54; 264/16–20
See application file for complete search history.

(56) References Cited

U.S. PATENT DOCUMENTS

| 4,389,496 A | 6/1983 | Leusner et al. |
| 4,708,649 A | 11/1987 | Millstein |
| 4,786,254 A | 11/1988 | Millstein et al. |
| 5,305,644 A | 4/1994 | Ehrreich |
| 5,381,799 A | 1/1995 | Hamilton et al. |
| 5,596,025 A | 1/1997 | Oxman et al. |
| 5,637,628 A | 6/1997 | Kamohara et al. |
| 5,732,721 A | 3/1998 | Pelok |
| 6,244,864 B1 | 6/2001 | Fujiwara et al. |
| 2002/0119424 A1 | 8/2002 | Margeas et al. |
| 2003/0190575 A1* | 10/2003 | Hilliard .......................... 433/6 |
| 2003/0203334 A1* | 10/2003 | Hedge et al. .................... 433/53 |
| 2005/0038180 A1* | 2/2005 | Jeans ............................ 524/588 |
| 2007/0166659 A1* | 7/2007 | Haase et al. .................... 433/37 |
| 2009/0285821 A1* | 11/2009 | Joens et al. .................. 424/139.1 |

FOREIGN PATENT DOCUMENTS

WO    WO/93/17654    9/1993

OTHER PUBLICATIONS

Rena T. Vakay and John C. Krois, "Universal Paradigms for Predictable Final Impressions", Compendium of Continuing Education in Dentistry, http://ce.compendiumlive.com/loadarticle.asp?quizid=32, pp. 1-10, 2008 AEGIS Communications, LLC.
Philip Millstein and Alvaro Maya, "An evaluation of occlusal contact marking indicators: A descriptive quantitative method", JADA, vol. 132, Sep. 2001, 1280-1286.
Leendert Boksman, Question 4—Journal of the Canadian Dental Association—"How do I minimize the amount of occlusal adjustment necessary for a crown?", Jul./Aug. 2005, vol. 71, No. 7, pp. 464-465.

* cited by examiner

*Primary Examiner* — Yogesh Patel
(74) *Attorney, Agent, or Firm* — Cesari and McKenna, LLP; William J. Mostyn, IV

(57) ABSTRACT

The occlusal position of a patient is measured by means of light transmission through a layer of a polysiloxane which is not cross-linked. This material forms an exceptionally accurate impression of a patient's bite essentially instantaneously and enables subsequent recording and analysis of the bite in a matter of minutes.

8 Claims, 2 Drawing Sheets

METHOD AND APPARATUS FOR OCCLUSAL POSITION MEASUREMENT AND RECORDING

CROSS-REFERENCE TO RELATED APPLICATIONS

The present application is a continuation-in-part of the following commonly assigned U.S. patent application Ser. No. 12/256,171, which was filed on Oct. 22, 2008 now U.S. Pat. No. 8,066,512, by Phillip L. Millstein and Edward W. Merrill for a METHOD FOR OCCLUSAL POSITION MEASUREMENT AND RECORDING and is hereby incorporated by reference.

FIELD OF THE INVENTION

The invention relates to the rapid and accurate measurement and recording of the occlusal position of a patient's teeth in connection with restorative and orthodontic dentistry.

BACKGROUND INFORMATION

An accurate measurement of the normal position of a patient's teeth is a critical factor in restorative and orthodontic procedures. A common technique for measuring the occlusal position is to make a mold of the teeth, or of the patient's bite, using a pliable material that can itself be hardened or that can be used to form a more nearly permanent cast. In this technique, the material is transformed into a stable gel from an initially soft plastic while in the mouth of the patient and over a period of a few minutes. The transformation can occur by chemical cross-linking or by physical gelation on cooling.

A different approach was described by one of the applicants herein in U.S. Pat. No. 4,786,254, issued Nov. 22, 1988, to Philip L. Millstein and Paul Goldberg for "Method Of Permanently Recording Occlusal Contacts". That patent describes a method of permanently documenting an occlusal position by having a patient bite down on a thin film of pliable impression material and thereafter forming a transmission photograph of the impression material. The technique has proven useful, but its accuracy is significantly affected by the particular material used to record the occlusal markings. The extent of variability of measurements made with various tapes and impression papers is discussed in detail in Millstein, Philip and Maya, Alvaro, "An evaluation of occlusal contact marking indicators", Journal of the American Dental Association, vol. 132, p. 1280, September 2001.

SUMMARY OF THE INVENTION

We have found that non-cross-linked (single-component) linear polysiloxanes having a molecular weight on the order of from 100,000 to 700,000 daltons, preferably from 100,000 to 500,000 daltons, provide superior impression material for occlusal measurement and recording systems, particularly systems using light transmission through the material as a measure of occlusal position. The material is advantageously provided as one or more thin layers (e.g., layers on the order of 1/16th to 1/8th inch) on a support in a retaining frame generally contoured to a patient's dental arch. The patient bites on the material to form the impression. Unlike prior materials, the material of the present invention need not cross-link, gell, or otherwise "set" before removal. Thus, an impression can be taken essentially instantaneously, and thereafter can be scanned and permanently recorded within a matter of minutes, even within the environment of an active dental practice.

Because of the rapidity of the process, the impression material does not have time to change its shape in any meaningful manner, and thus the impression can be recorded with high accuracy and faithfulness.

Our preferred material is a linear polydimethyl siloxane of the class known commercially as unfilled gum stock. Exemplary materials are the products SE30 and SE33 formerly sold by the General Electric Co. Advanced Materials Division, and now available from Momentive Performance Materials, Inc. Some gum stocks may contain vinyl groups and these can also be used as impression material, although the vinyl functionality is never employed in our invention because no cross-linking is involved. The polysiloxane material is physiologically inert. It offers little resistance to bite closure, and quickly and closely follows the contours of the teeth. It is fast: an accurate impression of occlusal position can be formed within about 10-15 seconds after application to a patient's teeth. Further, it is non-adhesive and is easily removable from the teeth without distortion after an impression is taken. Importantly, it retains its shape for at least a few minutes, which is more than sufficient for transfer to the measurement apparatus. Additionally useful are polydimethyl-covinylmethyl siloxane and polydimethyl-cophenylmethyl siloxane, also in the range of from 100,000 to 700,000 daltons molecular weight, preferably from 100,000 to 500,000 daltons. A small fraction of opacifying filler such as titanium dioxide, calcium carbonate, etc. may be added to the gum stock to provide enhanced contrast in subsequent evaluation of occlusal position by light transmission.

Cross-linkable polysiloxanes are commonly used as dental impression materials (see, e.g., WO/1993/017654 "Dental Impression materials Containing Quadrifunctional Siloxane Polymers") to form a bite replica in bulk, but not for thin-layer transmission measurement and recording. In contrast to the materials of the present invention, these materials must undergo a chemically-initiated cross-linking process while in the mouth of the patient in order to form a stable impression; this is typically accomplished by mixing together two different polysiloxanes, for example, one with some vinyl groups and the other with some silane hydrogen groups, and a catalyst. The resulting mixture is deployed into a trough appropriate to the patient's jaw and the filled trough is positioned over the teeth to take an impression. Inter-reaction of the two polysiloxane species in the presence of the catalyst leads to cross-linking and thus a durable shape. This takes several minutes and is often a source of discomfort for the patient, as well as a potential source of error in forming the impression. Our preferred materials, in contrast, do not utilize any additional component to set them by cross-linking, and do not become cross-linked at any time.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
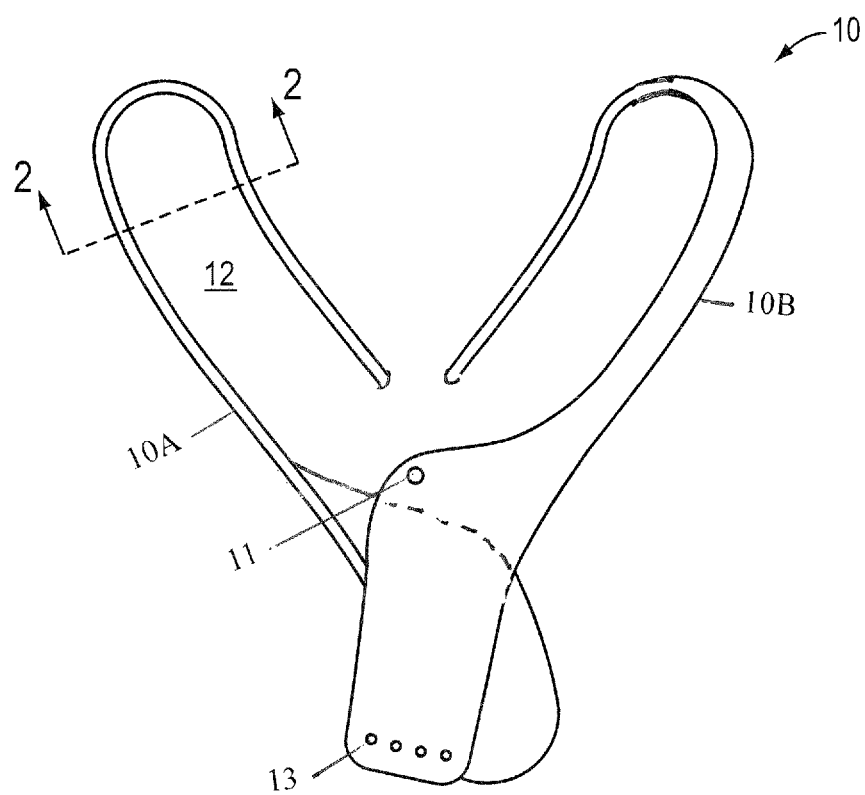
FIG. 1 is a plan view of a carrier holding a thin blanket of polysiloxane impression material for registering the occlusal position of a patient.

In FIG. 1, a frame 10 shaped to record the bite of a patient has a central area containing a blanket 12 of a single-component, linear, non-cross linking polysiloxane having a molecular weight on the order of from 100,000 to 700,000 daltons, preferably from 100,000 to 500,000 daltons, in accordance with the present invention. The frame is formed of two arms, 10A and 10B, which are overlapped at a pivot 11 to enable the arms to rotate toward and away from each other so as to accommodate the bite of a variety of patients. Pins 13 provide stops spreading the arms to different set positions.

By "single-component, linear, non-cross linking polysiloxane" we mean a linear polysiloxane that can receive an impression, and retain it for a suitable period of time, without the addition of other components that promote cross-linking. By "a suitable period of time", we mean a time of at least a few minutes.

The blanket is relatively thin (preferably on the order of from 1/16th inch to no more than 1/4 inch), and generally non-self-supporting. Thus, the frame preferably includes a support layer to assist in maintaining the polysiloxane within the frame. One example of a suitable frame for holding the polysiloxane material is a commercially available frame (sold under the mark "Premier") which has a number of filamentary threads forming a support layer in the form of a web or a felt of low density. The threads are of narrow diameter (e.g., preferably much less that the width of common human hair) and extended from the frame into the aperture. This form of support provides minimal resistance to forces applied to it, a desirable property when occlusal position is to be measured accurately without distortion caused by the measuring apparatus. It will be understood that other forms of support may be used, (e.g., a woven fabric of fine thread with low denier), as long as they can support the impression-receiving material yet offer minimal resistance to bite closure.

In accordance with the invention, a blanket of single-component polysiloxane, preferably linear polydimethyl siloxane, having a molecular weight on the order of from 100,000 to 700,000 daltons, preferably from 100,000 to 500,000 daltons, is fixed within the frame. This may be accomplished, for example, by applying thin sheets of the polysiloxane to opposite sides of a support layer that is attached to a frame; by casting the polysiloxane in situ onto opposite sides of the support layer; by preforming a blanket of the siloxane and support material and thereafter attaching it to the frame; or by other means. A polysiloxane layer on the order of approximately 1/16th to 1/8th inch thick on either or both sides of a support layer will usually be found adequate, although thicker or thinner layers may be used.

Until the material is actually used on a patient, it is desirably covered with a release layer, e.g., Teflon or other suitable material that is non-adherent to the polysiloxane. The material is also preferably enclosed in a fixture which confines the polysiloxane layer or layers within the holder and restricts their sagging or flowing. The fixture and then the release layers are removed and discarded just before insertion of the frame into the mouth of the patient.

Molecular weights less than 100,000 or greater than 500,000 may, of course, be used. However, as the molecular weight decreases, the ability of the polysiloxane material to hold its shape decreases. We believe that this is a consequence of the diminished number of entangling molecules in polysiloxanes of lower molecular weight. Conversely, as the molecular weight increases, the material becomes less pliable, and greater force is required to make an impression, thus possibly distorting the natural bite and also diminishing the accommodation of the material to the contours of the teeth.

Figure 2:
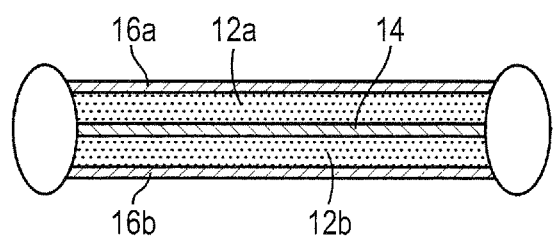
FIG. 2 is a view in cross section along the lines 2-2 of FIG. 1.

FIG. 2 is a cross-sectional view along the lines 2-2 of FIG. 1 showing one example of the resultant structure in more detail. The blanket 12 is formed of an upper polysiloxane layer 12a and a lower polysiloxane layer 12b, both adhered to an intermediate support layer 14. Release material 16a and 16b is applied to the upper (12a) and lower (12b) layers, respectively.

An occlusal impression is formed by removing the release layers and inserting the frame into a patient's mouth. When the patient bites down on the polysiloxane blanket, an impression of the patient's bite is rapidly formed: 10-15 seconds usually suffice to form an impression for purposes of thin-layer measurement and recording. Further, the impression is very accurate, a consequence, we believe, of the substantial free volume of polysiloxane, which allows flow of the material in response to small forces. Nonetheless, once an impression is formed, the material will retain the impression for at least several minutes, a period of time more than adequate to measure and record the impression, as will now be explained. After longer periods of time, the effects of gravity itself will gradually distort the impression.

Figure 3:
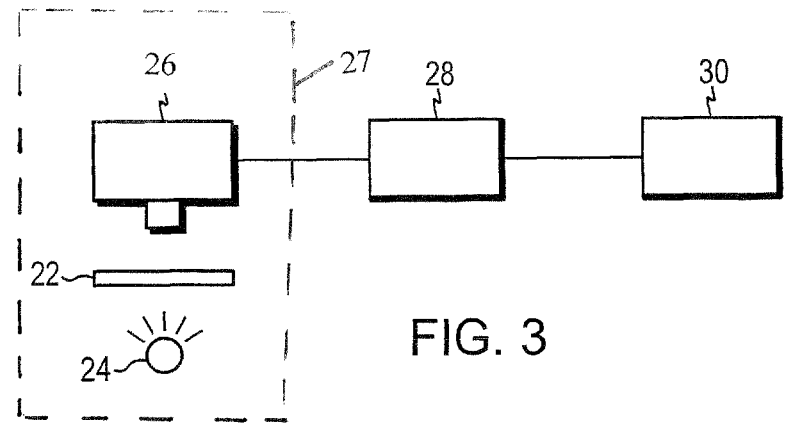
FIG. 3 is a schematic illustration of a measurement and recording system for measuring, recording, and analyzing occlusal impressions.

After the impression is formed, it is transferred to an analysis and recording station. As shown in FIG. 3, this comprises a camera 26 positioned above a mount for the frame which holds it while it is illuminated by a light source 24. In one embodiment, the mount comprises a transparent plate 22. The camera, plate, and light source are preferably enclosed in a housing 27 shown in outline form in FIG. 3. The camera 26 advantageously comprises a digital camera of suitable resolution, e.g., preferably 5 megapixels or more. The output of the camera (e.g., an image of the impression showing the light transmission through it) is electronically coupled to a processor 28, e.g., a personal computer. The output of the computer in turn is coupled to an output device 30, which may comprise one or more recording and/or inspection devices such as a storage device (e.g., a hard disk drive), a printer, a video display, or the like. The output device may store data in the form of either processed or unprocessed images In use, the frame or other carrier of the impression is placed on the transparent table 22 and is illuminated by the light source 24. Light transmitted through the impression is recorded by the camera 26 (e.g., as a still picture), and the resultant image is transmitted to the processor 28. The processor analyzes the image and forms a mapping of it in accordance with the translucency of the impression material. In one embodiment, we used ImageJ imaging software to map the image to gray-scale values. This software is available at http://rsb.info.nih.gov/ij/.

To enhance the readability of the resultant image, the gray scale values are preferably grouped into ranges of transmission, across the scale from 0% transmission to 100% transmission. For example, these ranges may encompass 0-10%, 10-20%, etc. All pixels within each range may then be exhibited with a single gray level to identify them and distinguish them from other areas, so that the dentist can immediately identify any areas of particular interest. To further enhance readability, the pixels within each range may be displayed in a color unique to the range.

Figure 4A:
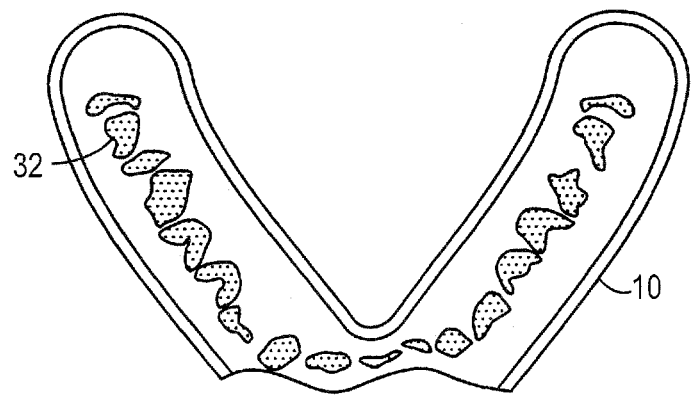
FIG. 4A is an image formed in accordance with the procedures described herein and recording the occlusal position of a sample bite.

FIG. 4A depicts an image formed in accordance with the procedures described herein. In particular, FIG. 4A depicts an image captured by the camera 26 after an impression of a patient's bite has been received in it and illuminated from below. The areas 32 record the areas of varying light transmission through the impression material caused by the varying depth of penetration of the teeth into the material. These areas will in fact exhibit differing gray scale values corresponding to different extents of occlusion, the lightest areas corresponding to maximal occlusion, the darkest to the least occlusion.

In order to display the various degrees of occlusion actually recorded in the image, the image is processed so as to group the transmission values into ranges of transmission, e.g., 0-10%, 10-20%, etc. Multiple ranges may be used to show differing extents of occlusion in the same image, with areas of minimum gray scale value indicating areas of maximal occlusion, and those of maximum gray scale values indicating minimal occlusion. Thus, the dentist can immediately discern areas of concern in establishing a proper bite. The ranges may advantageously be assigned different colors, corresponding to no occlusion at all to maximal occlusion, in order to enable rapid analysis by the dentist.

Figure 4B:
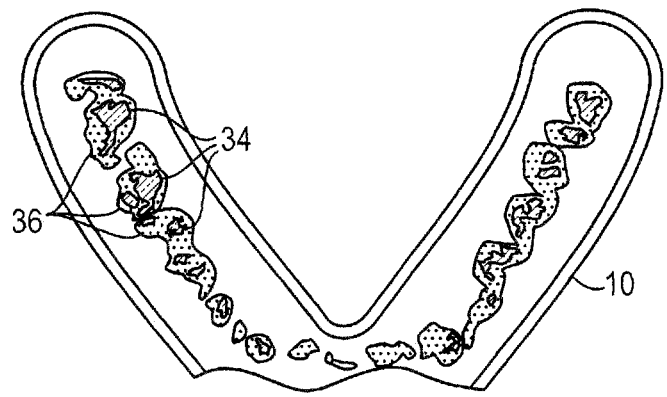
FIG. 4B shows the image of FIG. 4A after it has undergone contrast enhancement.

FIG. 4B depicts the image of FIG. 4A after the gray scale values of the image have been grouped into transmission ranges. For this purpose, ImageJ imaging software was used to map the original image to gray-scale values. For purposes of illustration, FIG. 4B shows only two ranges, e.g., a range corresponding to areas 34 of maximal occlusion and a range corresponding to areas 36 of lesser occlusion. From this image, the dentist can immediately discern areas where improvement of the bite is most needed.

Using the above procedure, an accurate and permanent record of the occlusal position of a patient can be formed in a dental office in a matter of minutes. The procedure is very comfortable for the patient, requiring only 10-15 seconds to form the impression. The impression is quickly analyzed, in a matter of minutes at most, so that the dentist can examine it while the patient is still in the dental chair and thereafter confer with the patient on a desired course of action if such is indicated by the results.

What is claimed is:

1. An apparatus for forming an impression of occlusal positions in a patient's bite suitable for subsequent examination by light transmission through the impression, comprising:
a frame configured for insertion into a patient's mouth, and
a single-component, linear, non-cross linked polysiloxane impression-receiving material having a molecular weight on the order of from 100,000 to 700,000 daltons supported by said frame configured for recording an impression of said bite without cross-linking said polysiloxane material.

2. The apparatus according to claim 1 in which said impression-receiving material comprises a polysiloxane having a molecular weight on the order of from 100,000 to 500,000 daltons.

3. The apparatus according to claim 1 in which said polysiloxane comprises polydimethyl siloxane.

4. The apparatus according to claim 1 in which said polysiloxane comprises poly-dimethylcovinylmethyl siloxane.

5. The apparatus according to claim 1 in which said polysiloxane comprises poly-dimethylcophenylmethyl siloxane.

6. The apparatus according to claim 1 in which said impression-receiving material includes an opacifying filler to enhance the contrast among impression-receiving areas when light is transmitted through said material.

7. The apparatus according to claim 1 which includes a support layer comprising a web of fine hairs extending from said frame to support said polysiloxane material in said frame.

8. The apparatus according to claim 1 which includes a support layer comprising a low denier woven fabric to support said polysiloxane material in said frame.

* * * * *